(12) United States Patent
Auclair et al.

(10) Patent No.: US 12,344,880 B2
(45) Date of Patent: Jul. 1, 2025

(54) MECHANOENZYMATIC DEGRADATION OF POLYMERS

(71) Applicant: THE ROYAL INSTITUTION FOR THE ADVANCEMENT OF LEARNING / MCGILL UNIVERSITY, Montréal (CA)

(72) Inventors: Karine Auclair, Laval (CA); Tomislav Friščić, Verdun (CA); Sandra Kaabel, Montréal (CA); James Patrick Therien, Montreal (CA)

(73) Assignee: THE ROYAL INSTITUTION FOR THE ADVANCEMENT OF LEARNING / MCGILL UNIVERSITY, Montréal (CA)

( * ) Notice: Subject to any disclaimer, the term of this patent is extended or adjusted under 35 U.S.C. 154(b) by 533 days.

(21) Appl. No.: 17/770,333

(22) PCT Filed: Oct. 27, 2020

(86) PCT No.: PCT/CA2020/051438
§ 371 (c)(1),
(2) Date: Apr. 20, 2022

(87) PCT Pub. No.: WO2021/081633
PCT Pub. Date: May 6, 2021

(65) Prior Publication Data
US 2022/0403422 A1 Dec. 22, 2022

Related U.S. Application Data

(60) Provisional application No. 62/926,738, filed on Oct. 28, 2019.

(51) Int. Cl.
*C08J 11/10* (2006.01)
*C12N 9/18* (2006.01)
*C12P 7/40* (2006.01)

(52) U.S. Cl.
CPC .............. *C12P 7/40* (2013.01); *C08J 11/105* (2013.01); *C12N 9/18* (2013.01); *C12Y 301/01074* (2013.01); *C08J 2367/02* (2013.01); *C08J 2367/04* (2013.01)

(58) Field of Classification Search
None
See application file for complete search history.

(56) References Cited

U.S. PATENT DOCUMENTS

| 9,476,073 | B2 | 10/2016 | Carbios |
| 10,124,512 | B2 | 11/2018 | Carbios |
| 10,287,561 | B2 | 5/2019 | Carbios et al. |
| 2019/0233803 | A1* | 8/2019 | Topham ................ C12N 9/18 |

FOREIGN PATENT DOCUMENTS

| WO | 2009005390 | 1/2009 |
| WO | 2014079844 A1 | 5/2014 |
| WO | 2017198786 | 11/2017 |
| WO | 2018157248 A1 | 9/2018 |

OTHER PUBLICATIONS

Brackmann, Rodrigo, et al. "Enzymatic Post-Consumer Poly(Ethylene Terephthalate) (PET) Depolymerization Using Commercial Enzymes." 3 Biotech, vol. 13, No. 5, 2023, pp. 135-135, https://doi.org/10.1007/s13205-023-03555-6. (Year: 2023).*

Kawai, Fusako, et al. "Current knowledge on enzymatic PET degradation and its possible application to waste stream management and other fields." Applied Microbiology and Biotechnology, vol. 103, No. 11, 2019, pp. 4253-4268, https://doi.org/10.1007/s00253-019-09717-y. (Year: 2019).*

Maurya, Ankita, et al. "Enzymatic Remediation of Polyethylene Terephthalate (PET)-Based Polymers for Effective Management of Plastic Wastes: An Overview." Frontiers in Bioengineering and Biotechnology, vol. 8, 2020, pp. 602325-, https://doi.org/10.3389/fbioe.2020.602325. (Year: 2020).*

F. Hammerer, L. Loots, J.-L. Do, J. P. D. Therien, C. W. Nickels, T. Friščić, K. Auclair, Angew. Chem. Int. Ed. 2018, 57, 2621 https://doi.org/10.1002/anie.201711643 (Year: 2018).*

Jbilou et al., A green method for polybutylene succinate recycling: Depolymerization catalyzed by lipase B from Candida antarctica during reactive extrusion, European Polymer Journal, Pergamon Press Ltd Oxford, GB, vol. 68, May 1, 2015 (May 1, 2015), pp. 207-215.

Hammerer, F. et al.: "Solvent-Free Enzyme Activity: Quick, High-Yielding Mechanoenzymatic Hydrolysis of Cellulose into Glucose". Angew. Chem. Int. Ed. 2018, 57, pp. 2621-2624.

Hammerer, F. et al.: "Rapid mechanoenzymatic saccharification of lignocellulosic biomass without bulk water or chemical pretreatment". The Royal Society of Chemistry: Green Chem. 2020, 22, pp. 3877-3884.

Kaabel, S. et al.: "Clean Enzymatic depolymerisation of highly crystalline polyethylene terephthalate in mois-solid reaction mixtures". bioRxiv. Jul. 2020.

Kaabel, S. et al.: "Mechanoenzymatic Transformations in the Absence of Bulk Water: A More Natural Way of Using Enzymes". ChemBioChem 2020, 21, pp. 742-758.

(Continued)

*Primary Examiner* — M Franco G Salvoza
*Assistant Examiner* — Benjamin Hall Easton
(74) *Attorney, Agent, or Firm* — Christian Cawthorn; NORTON ROSE FULBRIGHT CANADA LLP (57) ABSTRACT

A method of depolymerizing a polymer by combining together the polymer with an enzyme (a hydrolytic enzyme capable of catalyzing cleavage of said (CO)—O bond of an ester or carbonate linkage of the polymer) and an aqueous liquid to provide a reaction mixture. The polymer comprises a (CO)—O bond of an ester or carbonate linkage. The reaction mixture defines a ratio eta (η) of liquid volume, in μL, to total solids, in mg, that is less than 2 μL/mg. Then, allowing an enzyme-catalyzed reaction of the enzyme with the polymer to take place thereby forming a reaction product.

20 Claims, 2 Drawing Sheets

(56) References Cited

OTHER PUBLICATIONS

Kawai, F. et al.: "Current knowledge on enzymatic PET degradation and its possible application to waste stream management and other fields". Applied Microbiology and Biotechnology (2019) 103: pp. 4253-4268.
Navratilova, J. et al.: "Photodegradation of α-Nucleated Polypropylene" ANTEC 2009. pp. 624-643.
Ostadjoo, S. et al.: "Efficient Enzymatic Hydrolysis of Biomass Hemicellulose in the Absence of Bulk Water". Molecules 2019, 24, 4206.
Ronkvist, A.M. et al.: "Cutinase-Catalyzed Hydrolysis of Poly(ethylene terephthalate)". Macromolecules 2009, 42, pp. 5128-5138.
Therien, J.P.D., et al.: "Mechanoenzymatic Breakdown of Chitinous Material to N-Acetylglucosamine: The Benefits of a Solventless Environment". ChemSusChem 2019, 12, pp. 3481-3490.

* cited by examiner

MECHANOENZYMATIC DEGRADATION OF POLYMERS

TECHNICAL FIELD

This disclosure relates to a method for processing polymers.

BACKGROUND OF THE ART

Polymers are an integral part of many industries. They are used in many products, packaging, and manufacturing. Polyethylene terephthalate (PET) is one of the most commonly used polymers due to its mechanical and thermal properties. For example, PET is used in water bottles. PET, among other polyester, is difficult to degrade and therefore accumulates in the environment after use, thereby significantly contributing to environmental pollution. Microplastics, resulting from the leakage of plastic waste (composed of many polymers), are a threat to the marine wild life among other environments. Similarly, polycarbonates are durable polymers with a significant impact on the environment as they do not decompose easily.

To counter the pollution created by polymers, recycling has emerged to attempt to reduce the quantity of polymers deposited in the environment. However, recycling has significant limitations. For example, polyesters, such as PET, are recycled into lower-grade products, in a process termed downcycling. For example, PET used in a water bottle will be downcycled for use in carpets. Recycling PET into food grade products is challenging as it requires performing a depolymerisation at high temperatures and pressures with strong bases or acids. Furthermore, this depolymerisation process generates undesirable by-products.

There is therefore a need to improve the treatment of polymers after use.

SUMMARY

An aspect relates to a method of depolymerizing a polymer, said method comprising:
A) combining together the polymer with an enzyme and an aqueous liquid to provide a reaction mixture;
wherein said polymer is comprising a (CO)—O bond of an ester or carbonate linkage; wherein said reaction mixture is defining a ratio eta ($\eta$) of liquid volume, in µL, to total solids, in mg, that is less than 2 µL/mg;
said enzyme is a hydrolytic enzyme capable of catalyzing cleavage of said (CO)—O bond of an ester or carbonate linkage of said polymer;
B) allowing an enzyme-catalyzed reaction of said enzyme with said polymer to take place thereby forming a reaction product.

DETAILED DESCRIPTION

The term "depolymerization" as used herein means an enzyme-catalyzed reaction of the polymer providing a reaction product.

The term "reaction product" as used herein means a fragment of the polymer, a monomer of the polymer, an oligomer of the polymer, a residue (or subunit) of a monomer or any combination thereof, wherein said reaction product is also optionally recovered as a derivative such as an ester, an acid, an amide, a hydroxyl, and/or an aldehyde.

In one embodiment, the polymer is comprising at least a polyester, and/or a polycarbonate segment or chain. In one embodiment, the polymer is a polyester, or a polycarbonate.

In one embodiment, the polymer is an aliphatic polymer and in further embodiments, a homopolymer or copolymer.

In one embodiment, the polymer is semi-aromatic.

In one embodiment, the polymer is an aromatic copolymer.

In one embodiment, the homopolymer is an aromatic polyester selected from the group consisting of polyethylene terephthalate (PET), polybutylene terephthalate (PBT), polytrimethylene terephthalate (PTT), polyethylene naphthalate (PEN), and any combination thereof.

In one embodiment the aliphatic polymer is a polyester selected from the group consisting of polylactic acid or polylactide (PLA), polyglycolide (PGA), polycaprolactone (PCL), polyhydroxyalkanoate (PHA), polyhydroxybutyrate (PHB), polyethylene adipate (PEA), polybutylene succinate (PBS), and any combination thereof.

In one embodiment the polymer is a polyhydroxyalkanoate-type polymer for example poly(3-hydroxybutyrate-co-3-hydroxyvalerate) (PHBV).

In one embodiment the polymer is a copolymer, for example Vectran (copolymer of 4-hydroxybenzoic acid and 6-hydroxynaphthalene-2-carboxylic acid).

In one embodiment the polymer is in a form of powder, granule, film, cut or textile material.

In one embodiment the polymer is comprising a mixture of two or more different polymers.

The inventors have surprisingly discovered that moist-solid reaction mixtures enables the direct enzymatic depolymerization of polymers, in particular high crystallinity polymers, such as high crystallinity PET.

In a further embodiment, the polymer is PET.

In one embodiment, the PET has a crystallinity of at least 5%, at least 7%, at least 10%, at least 14%, at least 18%, at least 20%, at least 25%, at least 30%, at least 35%, at least 38%, at least 40%, at least 45%, at least 50%.

In one embodiment, the PET has a crystallinity of from about 0 to about 50%, from about 0 to about 45%, from about 0 to about 40%, from about 0 to about 38%, from about 0 to about 35%, from about 0 to about 30%.

In one embodiment, the PET has a crystallinity of from about 5 to about 50%, from about 7 to about 50%, from about 10 to about 50%, from about 14 to about 50%, from about 18 to about 50%, from about 20 to about 50%, from about 25 to about 50%.

Crystallinity can be measured by any method known to the person skilled in the art. For example, the crystallinity of PET can be determined by differential scanning calorimetry (DSC). DSC can be measured on differential scanning calorimeter instrument using standard 40 µL aluminum pans and samples in the range of 3 to 7 mg. A heat flux curve can be determined by heating the sample from 0° C. to 300° C. in 50 ml/min nitrogen flow, with a constant heating rate of 10° C./min. The enthalpies of melting ($\Delta H_m$, J/g) and cold crystallization ($\Delta H_c$, J/g) of a PET sample can be determined by integrating the areas under the corresponding peaks in the DSC scan. The crystallinity of PET can be determined according to the equation:

$$\% \text{ crystallinity} = \frac{(\Delta H_m - \Delta H_c)}{\Delta H_m^o} \cdot 100\%$$

where $\Delta H_m^o$ is the enthalpy of melting of a 100% crystalline polymer (140 J/g), and $\Delta H_m$ (J/g) and $\Delta H_c$ (J/g) are the experimentally measured enthalpies.

It was observed that an increase in the crystallinity of a polymer does not prevent the depolymerization of the polymer.

In one embodiment, the enzyme is a cutinase, esterase, lipase, PET hydrolase, PETase or any combination thereof.

In one embodiment, the enzyme is a cutinase, esterase, lipase, PETase or any combination thereof.

In one embodiment, the enzyme is any of a cutinase, a PETase, an esterase, a cutinase-like enzyme, a lipase or any combination thereof.

In one embodiment, the enzyme is a wild type or engineered cutinase from the organisms *Fusarium solani pisi* (*Nectaria haematococca*), *Thermobifida cellulosilytica*, *Thermobifida fusca*, *Thermobifida alba* or any combination thereof.

In one embodiment, the enzyme is a wild type or engineered cutinase-like enzyme from the organism *Saccharomonospora viridis*.

In one embodiment, the enzyme is a wild type or engineered esterase from the organisms *Thermobifida halotolerans*, *Bacillus subtilis*, *Penicillium citrinum* or any combination thereof.

In one embodiment, the enzyme is a wild type or engineered lipase from *Thermomyces lanuginosus*.

In one embodiment, the enzyme is a wild type or engineered PETase from organism *Ideonella sakaiensis*.

In one embodiment, the liquid is water and/or an aqueous buffer. The skilled person knows that different enzymes have different pH requirements for optimal performance and stability. Therefore, the skilled person knows the appropriate buffers to use in order to provide the desired catalytic reaction. For example, the buffer provides a specific pH and may be but is not limited to sodium phosphate buffer (herein also referred to as Na—PB), for example 0.1-1 M at pH 6 or 7.3, Tris-HCl buffer, for example at 1 M and a pH of 8.2, or bicine buffer, for example at 0.5 M and a pH of 9.

In certain embodiments, the buffer has a pH ranging from about 3 to about 9, preferably from 4.5 to about 7, more preferably from about 5 to about 7, and most preferably of about 5.

In one embodiment, the ratio of liquid-to-solids $\eta$ (in µL/mg) is less than about 2, less than about 1.9, less than about 1.8, less than about 1.7, less than about 1.6, less than about 1.5, less than about 1.4, less than about 1.3, less than about 1.2 or less than about 1.1. In another embodiment the ratio $\eta$ (in µL/mg) is from about 0.5 to about 2.0, from about 0.6 to about 2.0, from about 0.7 to about 2.0, from about 0.8 to about 2.0, from about 0.9 to about 2.0, from about 1.0 to about 2.0, from about 1.1 to about 2.0, about 1.2 to about 2.0, from about 1.3 to about 2.0, from about 1.4 to about 2.0, from about 1.5 to about 2.0, from about 1.6 to about 2.0, from about 1.7 to about 2.0, from about 1.8 to about 2.0, from about 1.9 to about 2.0, from about 0.5 to about 1.9, from about 0.5 to about 1.8, from about 0.5 to about 1.7, from about 0.5 to about 1.6, from about 0.5 to about 1.5, from about 1.2 to about 1.9, from about 1.3 to about 1.8, from about 1.4 to about 1.7, from about 1.4 to about 1.6, from about 1.5 to about 1.6, from about 1.6 to about 1.7, from about 1.4 to about 1.5.

In one embodiment, additives are added to facilitate the mechanochemical reaction.

In one embodiment, the step of combining to provide a reaction mixture is comprising a mechanical assistance in the form of milling, extrusion, resonance acoustic mixing, vortexing, grinding, or other methods of mixing solids, either intermittently, or continuously before said enzyme-catalyzed reaction.

In one embodiment, the step of combining to provide a reaction mixture is comprising mixing said reaction mixture before allowing the enzyme-catalyzed reaction to take place.

In one embodiment, the step of combining to provide a reaction mixture is comprising mixing or milling (preferably milling and more preferably ball milling) said reaction mixture before allowing the enzyme-catalyzed reaction to take place.

In one embodiment, the milling (such as by ball milling) of said reaction mixture before allowing the enzyme-catalyzed reaction to take place is for a duration of from about 5 minutes to about 30 minutes.

In one embodiment, the step of allowing the enzyme-catalyzed reaction to take place is optionally comprising a mechanical assistance in the form of milling, extrusion, resonance acoustic mixing, vortexing, grinding, or other methods of mixing solids, either intermittently, or continuously during said enzyme-catalyzed reaction and/or before said enzyme-catalyzed reaction.

In one embodiment, the step of allowing the enzyme-catalyzed reaction to take place is performed by ball milling.

Ball milling is known to the skilled person and may be conducted in reaction jars of different material (e.g. PTFE, stainless steel, zirconium oxide) in the presence of one of more balls of different size and material (e.g. tungsten carbide, stainless steel, PTFE-covered steel, zirconium oxide, agate), at frequencies ranging from 5-100 Hz, preferably between 10-30 Hz.

In one embodiment, the step of allowing the enzyme-catalyzed reaction to take place is performed by mixing.

In one embodiment, the step of allowing the enzyme-catalyzed reaction to take place is at a temperature of between about 0° C. to about 80° C., about 20° C. to about 70° C., about 30° C. to about 60° C., about 45° C. to about 55° C., or about 55° C.

In one embodiment, the step of allowing the enzyme-catalyzed reaction to take place is aging (i.e. without mechanical assistance such as mixing, milling, etc) at a temperature of between about 23° C. to about 60° C., about 30° C. to about 60° C., about 45° C. to about 55° C., or about 55° C.

In one embodiment, the aging is for a duration of from about 1 hour, about half a day (about 12 hours) or preferably about 1 day (about 24 hours), up to about 3 to 30 days.

In one embodiment, the method herein is comprising conducting at least twice a cycle of said steps of combining to provide a reaction mixture and the step of allowing the enzyme-catalyzed reaction to take place (preferably by aging). In particular, the method herein is comprising conducting at least one cycle, or three to 21 cycles.

In one embodiment, a next cycle is conducted before enzyme kinetics (i.e. during said step of allowing the enzyme-catalyzed reaction to take place—e.g. by aging)

reaches a plateau. The skilled person is capable of assessing the enzyme kinetics of a given pair of enzyme and polymer.

In one embodiment, before said step of combining together the polymer with said enzyme and said aqueous liquid, the method is further comprising milling (also referred to as "pre-milling" because the step is prior to the combining step) said polymer (for example PET), preferably said pre-milling is decreasing particle size of said polymer.

In one embodiment, said pre-milling is conducted in a jar (e.g. stainless steel jar) with balls (e.g. stainless steel ball) at an effective frequency (e.g. at 30 Hz). Said pre-milling may also be repeated in cycles (e.g. repeated cycles of about 5 to 10 min), thereby advantageously allowing the jar to return to room temperature between milling. In one embodiment, said reaction product is comprising at least a corresponding monomer unit of said polymer.

For greater clarity, the polymer used herein is other than a polysaccharide, the polysaccharide defined as polymeric carbohydrate molecule composed of long chains of monosaccharide units bound together by glycosidic bonds. Examples of polysaccharide include celluloses, hemicelluloses, chitin, chitosan, starch, glycogen, pectins, peptidoglycans, alginate, and combinations thereof.

In one embodiment, when said polymer is a polyester, said monomer unit is comprising the acid and/or ester form of said monomer.

In one embodiment, when said polymer is a polycarbonate, said monomer unit is comprising the forming diol monomer.

In one embodiment, when said polymer is an aliphatic polymer, said monomer unit is comprising the monomer unit in the form of acid. Examples include lactic acid, glycolic acid, hexanoic acid, and hydroxybutyric acid.

In one embodiment, when said polymer is an aliphatic polymer, the monomer unit of said polymer is in the form of acid and/or ester such as adipic acid/ethylene adipate and succinic acid/butylene succinate.

In one embodiment, when said polymer is comprising PET, said monomer unit in the form of acid and/or ester is comprising one or more of terephthalic acid (TPA), mono-2-hydroxyethyl terephthalate (MHET) and bis(2-hydroxyethyl) terephthalate (BHET).

In one embodiment, said monomer unit in the form of a diol is comprising bisphenol A (4,4'-(propane-2,2-diyl)diphenol), 1,1-bis(4-hydroxyphenyl)cyclohexane, di hydroxybenzophenone, tetrabromobisphenol A or tetramethylcyclobutanediol.

In one embodiment, when said polymer is comprising PTT, said monomer unit in the form of acid and/or ester is comprising one or more of terephthalic acid, 3-hydroxypropyl terephthalate and bis(3-hydroxypropyl) terephthalate.

In one embodiment, when said polymer is comprising PEN, said monomer unit in the form of acid and/or ester is comprising one or more of naphthalene-2,6-dicarboxylic acid, mono-2-hydroxyethyl naphthalate and bis(2-hydroxyethyl) naphthalate.

In one embodiment, when said polymer is comprising PHBV, said monomer unit in the form acid comprising one or more of 3-hydroxybutanoic acid and 3-hydroxypentanoic acid.

In one embodiment, the method further comprises after step B), a step of recovering said product.

In one embodiment, after step B), the method further comprises recovering the enzyme.

In one embodiment, the present method may degrade polyester from textiles and fibers, and/or mixed plastics.

Many further features and combinations thereof concerning the present improvements will appear to those skilled in the art following a reading of the instant disclosure.

EXAMPLES

TABLE 1

PET with different crystallinity.

| | Crystallinity of PET (measured by DSC) |
|---|---|
| Goodfellow powder PET (source A) | 38% |
| PET bottle, pre-milled (source B) | 36% |
| PET granules from Sigma-Aldrich, pre-milled (source D) | 24% |
| Goodfellow PET thin film, pre-milled (source C) | 22% |
| Goodfellow PET thin film, 0.5 × 0.5 cm squares (source C) | 13% |

Pre-Milling Conditions

The post-consumer PET bottle, post-consumer black PET container (80% recycled content) and low crystallinity PET film were cut into roughly 0.7×0.7 cm squares and pre-milled at 30 Hz in a 30 mL stainless steel jar, using a 15 mm stainless steel ball (11.6 g) to obtain a powder. The low crystallinity PET film was milled in installments of 10 min+5 min+5 min+10 min, to allow the jar to return to room temperature between milling. The crystallinity of all PET materials used was determined by differential scanning calorimetry.

Example I Polyester Degradation Using Cutinase

In a typical reaction, PET (300 mg, 1.58 mmol) was weighed into a 15 mL PTFE or stainless-steel jar, charged either with $ZrO_2$ or stainless-steel ball(s), to which the commercial enzyme preparation (300 μL, 1.95 mg protein) and buffer (150 μL) were added. The liquid-to-solid ratio is defined as η and expressed in μL $mg^{-1}$. The jar was then set to mill at a set frequency (generally 30 Hz) for 5 minutes. The resulting solids were aliquoted into three parts, 10-50 mg each, for analysis of the reaction products by HPLC at three time points: after milling, after milling followed by 3 days of aging at 55° C., and after milling followed by 7 days of aging at 55° C. Separate aliquots were prepared for PXRD and NMR analysis of the reaction products, and analyzed after 3 or 7 days of aging at 55° C. Specific reaction conditions and variations tested, together with corresponding hydrolysis yields are compiled into the following tables. After 7 days, the product can be extracted in methanol (2-5 mg/mL) with sonication (1-5 minutes), or preferably extracted in aqueous sodium carbonate before precipitation of the TPA product by acidification with HCl The resulting suspension was centrifuged for 5 min at 21.1×1000 g, after which the supernatant was analyzed by reverse phase high performance liquid chromatography with ultra-violet-visible and mass spectrometry detection (RP-HPLC-UV-MS).

Figure 1:
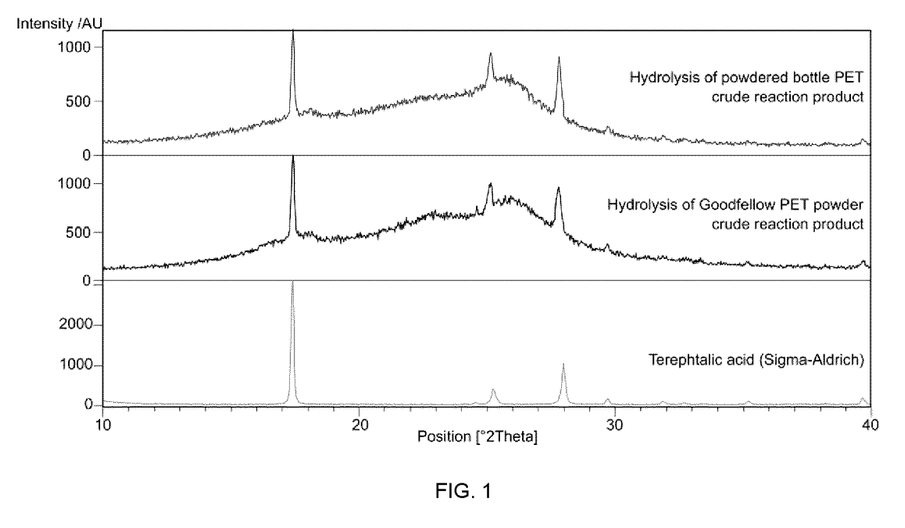
FIG. 1 is a graph of powder diffraction patterns showing the production of crystalline terephthalic acid in reaction mixtures.
Figure 2:
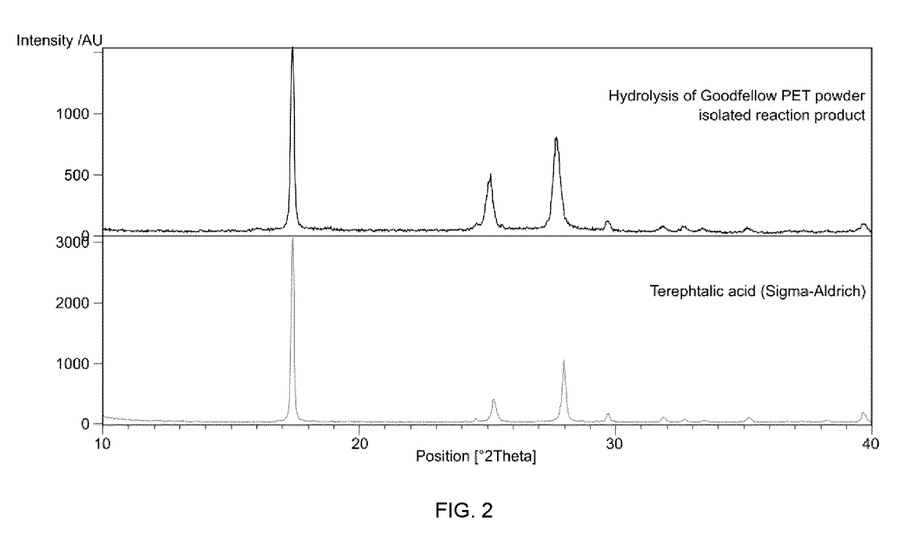
FIG. 2 is a graph of powder diffraction patterns of hydrolysis products.
Figure 3:
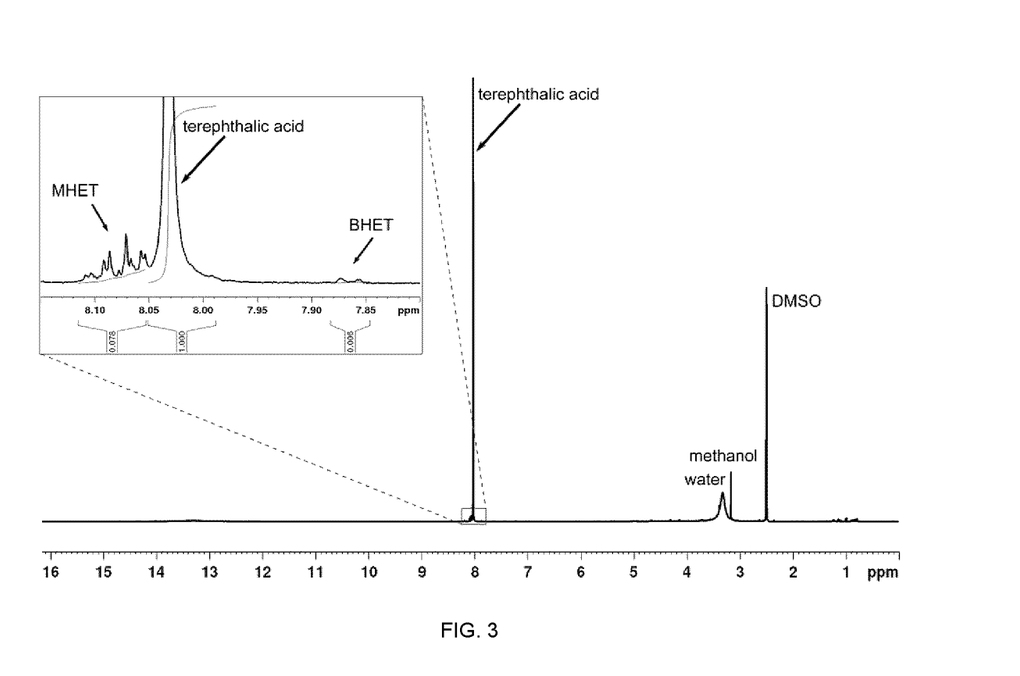
FIG. 3 is a $^1$H NMR spectrum of an enzymatic reaction mixture.

Powder X-ray diffraction (PXRD) analysis of the aged reaction mixtures (FIG. 1) showed the production of crystalline TPA in the solid samples. PXRD (FIG. 2) and nuclear magnetic resonance (NMR) analysis (FIG. 3) of the isolated hydrolysis products, extracted from the solids by repeated washing with methanol, showed that the product is mainly crystalline TPA, containing ≤5% of M HET and ≤1% of BHET.

The results are summarized in the following tables for the different sources of polyester.

DSC was measured on a Discovery 2500 Differential Scanning calorimeter from TA Instruments, using standard 40 µL aluminum pans and samples in the range of 3 to 7 mg. A heat flux curves was determined by heating the sample from 0° C. to 300° C. in 50 ml/min nitrogen flow, with a constant heating rate of 10° C./min. The enthalpies of melting ($\Delta H_m$, J/g) and cold crystallization ($\Delta H_c$, J/g) of a PET sample were determined by integrating the areas under the corresponding peaks in the DSC scan. The crystallinity of PET was determined according to the equation:

$$\% \text{ crystallinity} = \frac{(\Delta H_m - \Delta H_c)}{\Delta H_m^o} \cdot 100\%$$

where $\Delta H_m^o$ is the enthalpy of melting of a 100% crystalline polymer (140 J/g), and $\Delta H_m$ (J/g) and $\Delta H_c$ (J/g) are the experimentally measured enthalpies.

TABLE 1

Goodfellow powder PET (source A) depolymerisation via milling once followed by aging

| Enzyme | PET | Enzyme loading | Buffer (Materials, part III) | η (µL/mg) | Milling duration (min) | Aging temperature, duration | Yield of TPA (%) |
| --- | --- | --- | --- | --- | --- | --- | --- |
| | | 0 wt % (blank) | NaH$_2$PO$_4$/ Na$_2$HPO$_4$ pH 7.29 | 1.5 | 30 | 55° C., 7 days | 0.02 |
| Cutinase Novozym ® 51032 | Source A | 0.3 wt % | NaH$_2$PO$_4$/ Na$_2$HPO$_4$ pH 7.29 | 1.5 | 30 | 55° C., 7 days | 7.4 |
| Cutinase Novozym ® 51032 | Source A | 0.6 wt % | NaH$_2$PO$_4$/ Na$_2$HPO$_4$ pH 7.29 | 1.5 | 30 | 55° C., 7 days | 18.2 |
| Cutinase Novozym ® 51032 | Source A | 1.02 wt % | NaH$_2$PO$_4$/ Na$_2$HPO$_4$ pH 7.29 | 1.5 | 30 | 55° C., 7 days | 20.3 |
| Cutinase Novozym ® 51032 | Source A | 1.65 wt % | NaH$_2$PO$_4$/ Na$_2$HPO$_4$ pH 7.29 | 1.5 | 30 | 55° C., 7 days | 19.8 |
| Cutinase Novozym ® 51032 | Source A | 1.65 wt % | Tris-HCl pH 8.2 | 1.5 | 30 | 55° C., 7 days | 22.3 |
| Cutinase Novozym ® 51032 | Source A | 0.6 wt % | Water only | 1.5 | 30 | 55° C., 7 days | 10.2 |
| Cutinase Novozym ® 51032 | Source A | 0.6 wt % | NaH$_2$PO$_4$/ Na$_2$HPO$_4$ pH 7.29 | 1.5 | 5 | 55° C., 7 days | 20.8 |
| Cutinase Novozym ® 51032 | Source A | 0.6 wt % | NaH$_2$PO$_4$/ Na$_2$HPO$_4$ pH 7.29 | 1.5 | 10 | 55° C., 7 days | 17.2 |

A 16% yield of TPA was obtained when the solid-state reaction was started by simply mixing 0.3 g of the powdered PET with 0.3 mL of the cutinase enzyme solution and 0.150 mL of buffer, without milling, and aged for 7 days in a closed vial.

TABLE 2

Depolymerization of Goodfellow powder PET (source A) by milling once followed by aging in the presence of cutinase Novozym ® 51032

| Entry | PET (mg) | Buffer added | η (µL Enz. mg$^{-1}$) | Enz. Loading | Milling duration (min) | Aging temp. (° C.) | Aging duration (days) | Yield of TPA (%) |
| --- | --- | --- | --- | --- | --- | --- | --- | --- |
| 1 | 300 | 0.1M Na-PB pH 7.3[a] | 1.5 | 0.6 wt % | 0 | 55 | 7 | 19 ± 1 |
| 2 | 300 | 0.1M Na-PB pH 7.3 | 1.5 | 0.6 wt % | 5 | 55 | 7 | 20 ± 1 |
| 3 | 300 | 0.1M Na-PB pH 7.3 | 1.5 | 0.6 wt % | 5 | 35 | 7 | 8.0 ± 0.4 |
| 4 | 300 | 0.1M Na-PB pH 7.3 | 1.5 | 0.6 wt % | 5 | 40 | 7 | 14.8 ± 0.8 |
| 5 | 300 | 0.1M Na-PB pH 7.3 | 1.5 | 0.6 wt % | 5 | 45 | 7 | 23 ± 3 |
| 6 | 300 | 0.1M Na-PB pH 7.3 | 1.5 | 0.6 wt % | 5 | 50 | 7 | 24 ± 3 |

TABLE 2-continued

Depolymerization of Goodfellow powder PET (source A) by milling once followed by aging in the presence of cutinase Novozym® 51032

| Entry | PET (mg) | Buffer added | η (μL mg$^{-1}$) | Enz. Loading | Milling duration (min) | Aging temp. (° C.) | Aging duration (days) | Yield of TPA (%) |
|---|---|---|---|---|---|---|---|---|
| 7 | 300 | 0.1M Na-PB pH 7.3 | 1.5 | 0.6 wt % | 5 | 55 | 7 | 22.6 ± 0.9 |
| 8 | 300 | 0.1M Na-PB pH 7.3 | 1.5 | 0.6 wt % | 5 | 60 | 7 | 3.0 ± 0.4 |
| 9 | 300 | 0.1M Na-PB pH 7.3 | 1.5 | 0.6 wt % | 5 | 65 | 7 | 1.7 ± 0.2 |
| 10 | 300 | 0.1M Na-PB pH 6 | 1.5 | 0.6 wt % | 5 | 55 | 7 | 17 ± 1 |
| 11 | 300 | 0.1M Bicine pH 8 | 1.5 | 0.6 wt % | 5 | 55 | 7 | 17.9 ± 0.2 |
| 12 | 300 | 0.1M Bicine pH 9 | 1.5 | 0.6 wt % | 5 | 55 | 7 | 20 ± 1 |
| 13 | 300 | 0.5M Bicine pH 9 | 1.5 | 0.6 wt % | 5 | 55 | 7 | 24.6 ± 0.6[c] |
| 14 | 300 | 1M Tris-HCl pH 8.2 | 1.5 | 0.6 wt % | 5 | 55 | 7 | 21.0 ± 0.4 |
| 15 | 600 | 0.1M Na-PB pH 7.3 | 1.5 | 0.6 wt % | 5 | 55 | 7 | 19 ± 2 |

[a]0.1M sodium phosphate buffer, pH 7.3
[c]Reaction carried out in duplicate.

Remarkably, as seen in the table 2, manual mixing of the reactants instead of ball milling was enough to obtain TPA in 19±1% yield when it was followed by 7 days of aging (entry 1). The aging temperature can be modulated to affect the speed/yield, for example from above room temperature to 65° C., conveniently between about 30 to 65° C. or preferably from about 45 to 55° C. (Table 2 entries 3-9). This is in contrast to previously reported in-solution depolymerization of PET by cutinase Novozym® 51032, which is efficient only above the glass transition of the polymer. Further, the process remained at a similar level over a pH range of 6-9 (Table 2 entries 2, 10-12), regardless of the nature and concentration (0.1-1 M) of the buffer (Table 2 entries 13-14).

TABLE 3

Powdered cola bottle (PET source B)

| Enzyme | PET | Enzyme loading | Buffer (Materials, part III) | η (μL/mg) | Milling duration (min) | Aging temperature, duration | Yield of TPA (%) |
|---|---|---|---|---|---|---|---|
| | | 0 wt % (blank) | NaH$_2$PO$_4$/Na$_2$HPO$_4$ pH 7.29 | 1.5 | 30 | 55° C., 7 days | 0.01 |
| Cutinase Novozym® 51032 | Source B | 0.3 wt % | NaH$_2$PO$_4$/Na$_2$HPO$_4$ pH 7.29 | 1.5 | 30 | 55° C., 7 days | 6.4 |
| Cutinase Novozym® 51032 | Source B | 0.6 wt % | NaH$_2$PO$_4$/Na$_2$HPO$_4$ pH 7.29 | 1.5 | 30 | 55° C., 7 days | 17.1 |
| Cutinase Novozym® 51032 | Source B (0.5 × 0.5 cm squares) | 0.6 wt % | NaH$_2$PO$_4$/Na$_2$HPO$_4$ pH 7.29 | 1.5 | 30 | 55° C., 7 days | 17.6 |
| Cutinase Novozym® 51032 | Source B | 1.02 wt % | NaH$_2$PO$_4$/Na$_2$HPO$_4$ pH 7.29 | 1.5 | 30 | 55° C., 7 days | 19.05 |

TABLE 4

Goodfellow PET thin film (source C)

| Enzyme | PET | Enzyme loading | Buffer (Materials, part III) | η (μL/mg) | Milling duration (min) | Aging temp., duration | Yield of TPA (%) |
|---|---|---|---|---|---|---|---|
| Cutinase Novozym® 51032 | Source C (0.5 × 0.5 cm squares) | 1.02 wt % | NaH$_2$PO$_4$/Na$_2$HPO$_4$ pH 7.29 | 1.5 | 30 | 55° C., 7 days | 24 |

TABLE 4-continued

Goodfellow PET thin film (source C)

| Enzyme | PET | Enzyme loading | Buffer (Materials, part III) | η (μL/mg) | Milling duration (min) | Aging temp., duration | Yield of TPA (%) |
|---|---|---|---|---|---|---|---|
| Cutinase Novozym® 51032 | Source C (pre-milled) | 1.02 wt % | NaH$_2$PO$_4$/ Na$_2$HPO$_4$ pH 7.29 | 1.5 | 30 | 55° C., 7 days | 24 |

A 16% yield of TPA was obtained when the solid-state reaction according to Method was started from 0.5×0.5 cm squares of the thin film PET instead of the pre-milled powder. The squares did not get powdered by the milling process.

Figure 4:
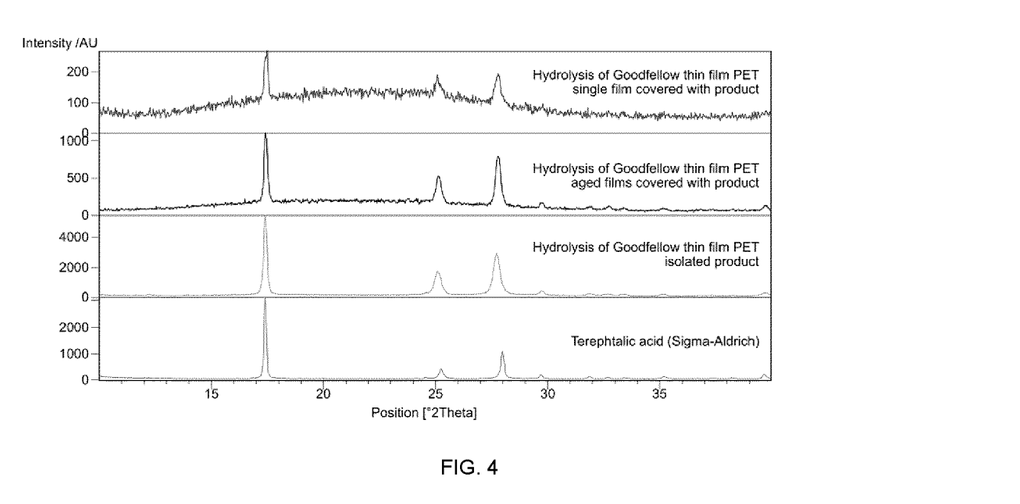
FIG. 4 is a graph of powder diffraction patterns of hydrolysis products.

A 11% yield of TPA was obtained when the solid-state reaction was started by simply covering 0.3 g of 0.5×0.5 cm squares cut from the thin film PET with 0.3 mL of the cutinase enzyme solution (giving 0.6 wt % enzyme loading) and 0.150 mL of sodium phosphate buffer (maintaining the same liquid-to-solid ratio), and aged for 7 days in a closed vial. Enzymatic action can be noticed by the appearance of the product TPA as white powder on the surface of the PET squares, confirmed by PXRD of one of the covered flakes (FIG. 4).

Method for the Reactive Aging Reactions (RAging)

In a typical RAging reaction, PET (source A, 300 mg, 1.58 mmol) was weighed into a 15 mL unsleeved PTFE jar, charged with a single 10 mm ZrO$_2$ ball (3.5 g), to which the commercial cutinase Novozym® 51032 preparation (300 μL, 1.95 mg protein) and buffer (150 μL) were added. A cycle of RAging typically consisted of ball milling at 30 Hz for 5 minutes followed by aging at 55° C. for 24 hours. These cycles were typically performed 7 times, with an aliquot (10-20 mg) collected at each cycle for analysis of the reaction products by HPLC. Sealing tape proved to be necessary to ensure that the jars remain closed during the aging step. Specific reaction conditions and variations tested, together with corresponding hydrolysis yields are compiled into Table 7.

TABLE 5

Powdered PET granules from Sigma (source D)

| Enzyme | PET | Enzyme loading | Buffer (Materials, part III) | η (μL/mg) | Milling duration (min) | Aging temperature, duration | Yield of TPA (%) |
|---|---|---|---|---|---|---|---|
| Cutinase Novozym® 51032 | Source D | 0.6 wt % | — | 1.0 | 30 | 55° C., 7 days | 3.5 |
| Cutinase Novozym® 51032 | Source D | 0.6 wt % | NaH$_2$PO$_4$/ Na$_2$HPO$_4$ pH 7.29 | 1.5 | 30 | 55° C., 7 days | 11.4 |
| Cutinase Novozym® 51032 | Source D | 0.6 wt % | Tris-HCl | 1.5 | 30 | 55° C., 7 days | 11.1 |

TABLE 6

Reactions with real life PET waste

| Entry | PET (mg) | PET source | Crystallinity (%) | Buffer added | η (μL mg$^{-1}$) | Enz. loading | Milling duration (min) | Aging temp. (° C.) | Aging duration (days) | Yield of TPA (%) |
|---|---|---|---|---|---|---|---|---|---|---|
| 1 | 300 | Bottle (pre-milled) | 31% | 0.1M Na—PB pH 7.3 [a] | 1.5 | 0.6 wt % | 30[b] | 55 | 7 | 16 ± 2 |
| 2 | 300 | Bottle squares | 30%[c] | 0.1M Na—PB pH 7.3 | 1.5 | 0.6 wt % | 30 | 55 | 7 | 15 ± 4 |
| 3 | 300 | Bottle + cap (pre-milled) | 31% [d] | 0.1M Na—PB pH 7.3 | 1.5 | 0.6 wt % | 30 | 55 | 7 | 19 [e] |
| 4 | 300 | Container, 80% rPET (pre-milled) | 34% | 0.1M Na—PB pH 7.3 | 1.5 | 0.6 wt % | 5 | 55 | 7 | 15. ± 1 |

[a] 0.1M sodium phosphate buffer, pH 7.3. [b]Reaction carried out in a 15 mL Teflon jar. [c]the higher error arises in part from the fact that the the bottle plastic varies in thickness. Pre-milled powder (that gives a lower error) is a better average of all the bottle parts, [d] Assumed based on the same PET pre-milling conditions as entry 1, the crystallinity of mixed polymer was not calculated based on the DSC curve (FIG. S3), [e] Reaction carried out in monoplicate.

TABLE 7

Conditions varied and results for the RAging reactions with cutinase Novozym ® 51032.

| Entry | PET (mg) | Buffer added | η (μL mg$^{-1}$) | Enz loading | RAging regime (milled + aged) | Number of cycles | Yield of TPA (%) |
|---|---|---|---|---|---|---|---|
| 1 | 300 | 0.1M Na—PB pH 7.3 [a] | 1.5 | 0.6 wt % | 5 min + 1 day 55° C. | 3 | 21 ± 2 |
|   |     |                       |     |          |                      | 7 | 22 ± 3 |
| 2 | 900 | 0.1M Na—PB pH 7.3 | 1.5 | 0.6 wt % | 5 min + 1 day 55° C. | 3 | 21.5 ± 0.5 |
|   |     |                   |     |          |                      | 7 | 26 ± 2 |
| 3 | 300 |                   | 1.5 | 2.6 wt % | 5 min + 1 day 55° C. | 3 | 18 ± 2 |
|   |     |                   |     |          |                      | 7 | 18 ± 2 |
| Multi-round reaction, washing out the products and adding fresh commercial enzyme after every 3 cycles ||||||||
| 4 | 900 | 0.1M Na—PB pH 7.3 | 1.5 | 0.6 wt % | 5 min + 1 day 55° C. | 3 | 17.0 ± 0.6 |
|   |     |                   |     | 1.2 wt % |                      | 6 | 26 ± 1 |
|   |     |                   |     | 1.7 wt % |                      | 9 | 31 ± 1 |
|   |     |                   |     | 2.0 wt % |                      | 12 | 36 ± 2 |
|   |     |                   |     | 2.4 wt % |                      | 15 | 41 ± 2 |
|   |     |                   |     | 2.6 wt % |                      | 18 | 45 ± 2 |
|   |     |                   |     | 2.8 wt % |                      | 21 | 49 ± 2 |
| Multi-round reaction, adding lyophilized enzyme after every 3 cycles ||||||||
| 5 | 300 | 0.1M Na—PB pH 7.3 | 1.5 | 0.6 wt % | 5 min + 1 day 55° C. | 3 | 8.6 ± 0.5 |
|   |     |                   |     | 1.3 wt % |                      | 6 | 16.4 ± 0.2 |
|   |     |                   |     | 2.0 wt % |                      | 9 | 20 ± 2 |
|   |     |                   |     | 2.6 wt % |                      | 12 | 23 ± 1 |
|   |     |                   |     | 3.3 wt % |                      | 15 | 26 ± 1 |
|   |     |                   |     | 3.9 wt % |                      | 18 | 33 ± 2 |
|   |     |                   |     | 4.6 wt % |                      | 21 | 38 ± 1 |

[a] 0.1M sodium phosphate buffer, pH 7.3..

The above process led to a 21±2% yield of TPA in only 3 days (Table S6 entry 1), compared to 7 days needed to achieve the same yield if milling was performed only once. The RAging reaction was also successfully scaled up 3-fold, using the same 15 mL milling jars, without any decrease in conversion (Table 7 entry 2). A 4-fold increase in enzyme loading brought no improvement in TPA yield (Table 7 entry 3).

Alternatively, another portion of enzyme can be added after every 3-cycle of RAging after washing the products off, resulting in 10% additional yield of TPA from the remaining PET at each round of addition, allowing to reach an overall 49±2% yield of TPA from 900 mg of PET over 7 rounds (7 rounds of 3 cycles, for a total of 21 cycles), using a total of 3 wt % of enzyme (Table 7 entry 4). A similar multi-round RAging experiment without product removal and with the enzyme added as a lyophilized powder (at constant η=1.5 μL mg-1) yielded 38±1% TPA (Table 7 entry 5), suggesting that washing increases PET surface accessibility for the added fresh enzyme.

TABLE 8

Powdered poly-3-hydroxybutyrate (PHB)

| Enzyme | Enzyme loading | Buffer (Materials, part III) | η (μL/mg) | Milling duration (min) | Aging temperature, duration | Yield of poly-3-hydroxy-butyrate (%) |
|---|---|---|---|---|---|---|
| (none) |  | NaHPO$_4$/Na$_2$HPO$_4$ pH 7.29 | 1.5 | 5 | 55° C., 3 days | 2.6% |
| Cutinase Novozym ® 51032 | 0.6 wt % | NaH$_2$PO$_4$/Na$_2$HPO$_4$ pH 7.29 | 1.5 | 5 | 55° C., 3 days | 6.8% |

TABLE 9

Powdered polycarbonate (PC; granules from Millipore Sigma)

| Enzyme | Enzyme loading | Buffer (Materials, part III) | η (μL/mg) | Milling duration (min) | Aging temperature, duration | Yield of bisphenol A (%) |
|---|---|---|---|---|---|---|
| (none) |  | NaHPO$_4$/Na$_2$HPO$_4$ pH 7.29 | 1.5 | 5 | 55° C., 3 days | Not detected |
| Cutinase Novozym ® 51032 | 0.6 wt % | NaH$_2$PO$_4$/Na$_2$HPO$_4$ pH 7.29 | 1.5 | 5 | 55° C., 3 days | 2.0 |

TABLE 9-continued

Powdered polycarbonate (PC; granules from Millipore Sigma)

| Enzyme | Enzyme loading | Buffer (Materials, part III) | η (µL/mg) | Milling duration (min) | Aging temperature, duration | Yield of bisphenol A (%) |
|---|---|---|---|---|---|---|
| Cutinase Novozym® 51032 | 0.6 wt % | NaH$_2$PO$_4$/ Na$_2$HPO$_4$ pH 7.3 | 1.5 | 30 | 55° C., 7 days | 3.81 |

TABLE 10 polybutylene terephthalate (PBT, pellets from Millipore Sigma)

| Enzyme | Enzyme loading | Buffer (Materials, part III) | η (µL/mg) | Milling duration (min) | Aging temperature, duration | Yield of TPA (%) |
|---|---|---|---|---|---|---|
| Cutinase Novozym® 51032 | 0.6 wt % | NaHPO$_4$/ Na$_2$HPO$_4$ pH 7.3 | 1.5 | 30 | 55° C., 7 days | Not detected |

The enzyme activity was evaluated after aging with polybutylene terephthalate (PBT), a material that structurally resembles PET. Despite the fact that PBT is a poorer substrate ca. 1% PBT hydrolysis was observed after 3 or 7 days of aging.

Table 11 shows results for varied reaction conditions using the lyophilized enzyme. The commercial cutinase Novozym® 51032 was lyophilized using a Labconco FreeZone 1 Liter Benchtop Freeze Dry System.

TABLE 11

Conditions varied and results for the reactions using the lyophilized enzyme on source A PET.

| Entry | PET (mg) | Buffer added | η (µL mg$^{-1}$) | Enz. Loading[a] | Milling duration (min) | Aging temp. (° C.) | Aging duration (days) | Yield of TPA (%) |
|---|---|---|---|---|---|---|---|---|
| 1 | 300 | 1M Tris-HCl pH 8.2 | 1.5 | 0.6 wt % (lyo) | 5 | 55 | 7 | 18 ± 3[b] |
| 2 | 300 | MilliQ water only | 0.5 | 0.6 wt % (lyo) | 5 | 55 | 7 | 13.2 ± 0.4 |
| 3 | 300 | MilliQ water only | 1.0 | 0.6 wt % (lyo) | 5 | 55 | 7 | 15 ± 1 |
| 4 | 300 | MilliQ water only | 1.5 | 0.6 wt % (lyo) | 5 | 55 | 7 | 14.5 ± 0.6 |
| 5 | 300 | MilliQ water only | 2.0 | 0.6 wt % (lyo) | 5 | 55 | 7 | 15.0 ± 0.6 |
| 6 | 300 | 0.1M Na—PB pH 7.3 + MilliQ[c] | 0.5 | 0.6 wt % (lyo) | 5 | 55 | 7 | 15.4 ± 0.3 |
| 7 | 300 | 0.1M Na-PB pH 7.3 + MilliQ[d] | 1.0 | 0.6 wt % (lyo) | 5 | 55 | 7 | 14 ± 1 |
| 8 | 300 | 0.1M Na—PB pH 7.3 + MilliQ[e] | 1.5 | 0.6 wt % (lyo) | 5 | 55 | 7 | 18 ± 1 |
| 9 | 300 | 0.1M Na—PB pH 7.3 + MilliQ[f] | 2.0 | 0.6 wt % (lyo) | 5 | 55 | 7 | 14.5 ± 0.8 |

[a]16-17 mg of the lyophilized powder was used per reaction which contains 12 wt % cutinase Novozym® 51032, 11 wt % Tris-HCl pH 7.3 buffer and 89 wt % NaCl [b]Reaction carried out in duplicate, [c]75 µL of 0.1M sodium phosphate buffer and 75 µL of water, [d]150 µL of 0.1M sodium phosphate buffer and 150 µL of water, [e]150 µL of 0.1M sodium phosphate buffer and 300 µL of water, [f]150 µL of 0.1M sodium phosphate buffer and 450 µL of water.

A reaction using a buffer-exchanged lyophilized enzyme powder led to 18±3% TPA yield (Table 11 entry 1), confirming that the reaction is catalysed by the enzyme and not by other components of the commercial enzyme solution. Varying the liquid-to-solid ratio between 0.5–2 µL mg$^{-1}$ (Table 11 entries 6-9) demonstrated that the enzyme functions well even in drier conditions, allowing STY of 1.58 gTPA L$^{-1}$ h$^{-1}$. This is remarkable, considering that a liquid-to-solid ratio η=0.5 µL mg$^{-1}$ corresponds to only 2-fold molar excess of water in the enzyme-catalysed PET hydrolysis.

In conclusion, without a bulk solvent and by using a solid moist reaction mixture, the present method demonstrates the activity of the cutinase to degrade polyester from various sources with mild reagents and conditions. The present method yields a clean product with minimal waste, and because of a smaller reaction volume has generally an easier manipulation than methods from the prior art.

Example II Polyester Degradation Using PETase Enzyme

First, 0.3 g of the powdered PET (source A), 10 mg of recombinant PETase enzyme from *Ideonella sakaiensis*, expressed in *E. coli* with a C-terminal histidine tag, purified lyophilized powder (giving 1 wt % enzyme loading), 100 mg of PEG solid additive (polyethylene glycol 8000, purchased from Sigma-Aldrich) and 0.35 mL of bicine buffer (0.5 M and pH 9 prepared from 4.1 g of bicine in 15 mL of milliQ water, adjusted to the final pH 9 by dropwise addition of HCl (aq, 37%) and then diluted to the final volume of 50 mL) measured into a 15 mL Teflon-lined milling jar containing a single 10 mm $ZrO_2$ ball bearing and milled at 30 Hz frequency for 5 minutes. The total ratio of liquid-to-solids added to the milling jar, expressed as η, was η=1.13 µL/mg. The resulting solid reaction mixture was further allowed to react through heating at 70° C. without mixing for 7 days (aging). After 7 days, the product mixture was suspended in methanol (2-5 mg/mL) and sonicated for 1-5 minutes. The resulting suspension was centrifuged for 5 min at 21.1×1000 g, after which the supernatant was analyzed by reverse phase high performance liquid chromatography with ultra-violet-visible and mass spectrometry detection (RP-HPLC-UV-MS). The results are summarized in Table 12. The experiment was then repeated with controls consisting of no enzyme and heat inactivated enzyme. The results are summarized in Table 13.

In conclusion, without a solvent and by using a solid moist reaction mixture, the present method demonstrates the activity of PETase to degrade polyester with mild reagents and conditions. The present method yields a clean product with minimal waste, and because of a smaller reaction volume has generally an easier manipulation than methods from the prior art.

Example III Polyester Degradation Using Esterase Enzyme

First, 0.3 g of powdered PET from source D, 51 mg of esterase powder (giving 10 wt % enzyme loading) from porcine liver (EC 3.1.1.1, lyophilized powder, 15 KLU/g, protein content 60 wt %), purchased from Sigma Aldrich (CAS 9016-18-6), used as received, and 0.3 mL of milliQ water were measured into a 15 mL Teflon-lined milling jar containing a single 10 mm $ZrO_2$ ball bearing and then milled at 30 Hz frequency for 30 minutes. The total ratio of liquid-to-solids added to the milling jar, expressed as η, was η=1.0 µL/mg. The resulting moist solid reaction mixture was further allowed to react through heating at 55° C. without mixing for 7 days (aging). After 7 days, the product mixture was suspended in methanol (2-5 mg/mL) and sonicated for 1-5 min. The resulting suspension was centrifuged for 5 min at 21.1×1000 g, after which the supernatant was analyzed by reverse phase high performance liquid chromatography with ultra-violet-visible and mass spectrometry detection (RP-HPLC-UV-MS). The results are summarized in Table 14.

TABLE 12

PETase results

| Enzyme | PET | Enzyme loading | Buffer (Materials, part III) | η (µL/mg) | Milling duration (min) | Aging temperature, duration | Yield of TPA (%) |
|---|---|---|---|---|---|---|---|
| PETase | Source A | 1 wt % | Bicine, pH 9 | 1.13 | 5 | 70° C., 7 days | 5 |

TABLE 13

PETase results with controls

| Enzyme | PET | Enzyme loading | Buffer (Materials, part III) | Additive | η (µL/mg) | Milling duration (min) | Aging temperature, duration | Yield of TPA (%) |
|---|---|---|---|---|---|---|---|---|
|  | Source A | 0 wt % (blank) | Bicine, pH 9 | 100 mg PEG8000 | 1.13 | 5 | 70° C., 7 days | 0.05 |
| Heat-inactivated PETase | Source A | 1 wt % | Bicine, pH 9 | 100 mg PEG8000 | 1.13 | 5 | 70° C., 7 days | 0.05 |
| PETase | Source A | 1 wt % | Bicine, pH 9 | 100 mg PEG8000 | 1.13 | 5 | 70° C., 7 days | 5 |

TABLE 14

Esterase results

| Enzyme | PET | Enzyme loading | Buffer (Materials, part III) | η (μL/mg) | Milling duration (min) | Aging temperature, duration | Yield of TPA (%) |
|---|---|---|---|---|---|---|---|
| (none) | | 0 wt % (blank) | water | 1.0 | 30 | 55° C., 7 days | 0.0 |
| esterase | Source D | 5 wt % | water | 0.5 | 30 | 55° C., 7 days | 0.02 |
| esterase | Source D | 5 wt % | water | 1.0 | 30 | 55° C., 7 days | 0.34 |
| esterase | Source D | 5 wt % | water | 1.5 | 30 | 55° C., 7 days | 0.18 |
| esterase | Source D | 10 wt % | water | 1.0 | 30 | 55° C., 7 days | 0.37 |

As can be seen in Table 14, the enzymatic activity was again confirmed with the present method with mild reagents and conditions. The present method yields a clean product with minimal waste, and because of a smaller reaction volume has generally an easier manipulation than methods from the prior art.

Furthermore, as can be seen in the examples, the present method is selective towards the hydrolysis product TPA, compared to prior art reports on PETase and its mutants, which report MHET as the major product.

Example IV Method of Depolymerizing a Polymer in the Form of Textile

The method allowed for the enzymatic depolymerization of a polymer in the form of textile into its corresponding monomers. As described above, this was either carried out by combined ball milling and incubating of the solid reaction mixture, or by simple mixing and incubating of the solid reaction mixture. After the incubation, the reaction mixture was analyzed for the hydrolysis products (e.g. TPA, and MHET) by extracting the products and analyzing the supernatant by RP-HPLC-UV-MS.

Results (Method of Only Milling+Aging):

Powdered textile (preferred) or squares cut from a textile are placed into the milling jar with a milling ball, to which the enzyme solution and small amount of buffer (or water) is added, in a total liquid-to-solid ratio below 2 μL/mg. The mixture is milled for 5 or 30 minutes at 30 Hz, after which the mixture is incubated for 7 days at 55° C.

A. Dark blue post-consumer polyester textile—100% polyester based on label, polyester identified as PET based on differential scanning calorimetry (melting point).

TABLE 15

| Enzyme | Pre-milled? | Enzyme loading | Buffer (Materials, part III) | η (μL/mg) | Milling duration (min) | Aging temperature, duration | Yield of TPA (%) |
|---|---|---|---|---|---|---|---|
| Cutinase Novozym® 51032 | no | 0.6 wt % | NaH$_2$PO$_4$/Na$_2$HPO$_4$ pH 7.29 | 1.5 | 10 | 55° C., 7 days | 3.1 ± 1.1 |
| Cutinase Novozym® 51032 | no | 0.6 wt % | NaH$_2$PO$_4$/Na$_2$HPO$_4$ pH 7.29 | 1.5 | 30 | 55° C., 7 days | 6.3 ± 0.1 |
| Cutinase Novozym® 51032 | Yes, 30 min at 30 Hz | 0.6 wt % | NaH$_2$PO$_4$/Na$_2$HPO$_4$ pH 7.29 | 1.5 | 5 | 55° C., 7 days | 8.8 ± 0.2 |

B. Light beige post-consumer polyester textile—65% polyester and 35% viscose based on label, polyester identified as PET based on differential scanning calorimetry (melting point).

TABLE 16

| Enzyme | Pre-milled? | Enzyme loading | Buffer (Materials, part III) | η (μL/mg) | Milling duration (min) | Aging temperature, duration | Yield of TPA (%) |
|---|---|---|---|---|---|---|---|
| Cutinase Novozym® 51032 | no | 0.6 wt % | NaH$_2$PO$_4$/Na$_2$HPO$_4$ pH 7.29 | 1.5 | 10 | 55° C., 7 days | 1.4 ± 0.1 |
| Cutinase Novozym® 51032 | Yes, 30 min at 30 Hz | 0.6 wt % | NaH$_2$PO$_4$/Na$_2$HPO$_4$ pH 7.29 | 1.5 | 5 | 55° C., 7 days | 8.2 ± 0.2 |

Results (Method of RAging):

Powdered textile is placed into the milling jar with a milling ball, to which the enzyme solution and small amount of buffer (or water) is added, in a total liquid-to-solid ratio below 2 µL/mg. The mixture is milled for 5 minutes at 30 Hz, after which the mixture is incubated for 24 hours at 55° C. This cycle of milling and incubating is repeated, with a small aliquot removed after each cycle to test for the conversion of TPA.

A. Light beige post-consumer polyester textile—65% polyester and 35% viscose based on label, polyester identified as PET based on differential scanning calorimetry (melting point).

TABLE 17

| Enzyme | Pre-milled? | Enzyme loading | Buffer (Materials, part III) | η (µL/mg) | RAging conditions (milling + aging) | Number of cycles | Yield of TPA (%) |
|---|---|---|---|---|---|---|---|
| Cutinase Novozym ® 51032 | Yes, 30 min at 30 Hz | 0.6 wt % | $NaH_2PO_4$ / $Na_2HPO_4$ pH 7.29 | 1.5 | 5 min 30 Hz + 24 h at 55 C. | 6 | 8.0 ± 1.0 |

B. White polyester lining textile (Fabricville)—100% polyester based on label, confirmed by acid hydrolysis test (textile exposed for 1 h at room temperature to 70% $H_2SO_4$ aq. solution, which hydrolyses the cotton, then remaining solids are dried and weighed to determine the PET content), polyester identified as PET based on differential scanning calorimetry (melting point).

TABLE 18

| Enzyme | Pre-milled? | Enzyme loading | Buffer (Materials, part III) | η (µL/mg) | RAging conditions (milling + aging) | Number of cycles | Yield of TPA (%) |
|---|---|---|---|---|---|---|---|
| Cutinase Novozym ® 51032 | Yes, 40 min at 30 Hz | 0.6 wt % | $NaH_2PO_4$ / $Na_2HPO_4$ pH 7.29 | 1.5 | 5 min 30 Hz + 24 h at 55 C. | 6 | 12.2 |
| Cutinase Novozym ® 51032 | Yes, 60 min at 30 Hz | 0.6 wt % | $NaH_2PO_4$ / $Na_2HPO_4$ pH 7.29 | 1.5 | 5 min 30 Hz + 24 h at 55 C. | 6 | 14.8 |

C. White polyester/cotton blend textile—Buckram (Fabricville)—80% polyester and 20% cotton based on label, acid hydrolysis test indicates 85% polyester and 15% cotton (textile exposed for 1 h at room temperature to 70% $H_2SO_4$ aq. solution, which hydrolyses the cotton, then remaining solids are dried and weighed to determine the PET content), polyester identified as PET based on differential scanning calorimetry (melting point).

TABLE 19

| Enzyme | Pre-milled? | Enzyme loading | Buffer (Materials, part III) | η (µL/mg) | RAging conditions (milling + aging) | Number of cycles | Yield of TPA (%) |
|---|---|---|---|---|---|---|---|
| Cutinase Novozym ® 51032 | Yes, 40 min at 30 Hz | 0.6 wt % | $NaH_2PO_4$ / $Na_2HPO_4$ pH 7.29 | 1.5 | 5 min 30 Hz + 24 h at 55 C. | 6 | 7.0 |
| Cutinase Novozym ® 51032 | Yes, 60 min at 30 Hz | 0.6 wt % | $NaH_2PO_4$ / $Na_2HPO_4$ pH 7.29 | 1.5 | 5 min 30 Hz + 24 h at 55 C. | 6 | 6.8 |

D. White polyester/cotton blend textile—Broadcloth (Fabricville)—65% polyester and 35% cotton based on label, acid hydrolysis test indicates 70% polyester and 30% cotton (textile exposed for 1 h at room temperature to 70% $H_2SO_4$ aq. solution, which hydrolyses the cotton, then remaining solids are dried and weighed to determine the PET content), polyester identified as PET based on differential scanning calorimetry (melting point).

TABLE 20

| Enzyme | Pre-milled? | Enzyme loading | Buffer (Materials, part III) | η (μL/mg) | RAging conditions (milling + aging) | Number of cycles | Yield of TPA (%) |
|---|---|---|---|---|---|---|---|
| Cutinase Novozym ® 51032 | Yes, 40 min at 30 Hz | 0.6 wt % | NaH$_2$PO$_4$/ Na$_2$HPO$_4$ pH 7.29 | 1.5 | 5 min 30 Hz + 24 h at 55 C. | 6 | 16.2 |
| Cutinase Novozym ® 51032 | Yes, 60 min at 30 Hz | 0.6 wt % | NaH$_2$PO$_4$/ Na$_2$HPO$_4$ pH 7.29 | 1.5 | 5 min 30 Hz + 24 h at 55 C. | 6 | 15.7 |

As can be seen therefore, the examples described above and illustrated are intended to be exemplary only. The scope is indicated by the appended claims.

What is claimed is:

1. A method of depolymerizing a polymer, said method comprising:
   A) combining together the polymer with an enzyme and an aqueous liquid to provide a reaction mixture; wherein said polymer comprises a (CO)—O bond of an ester or carbonate linkage; wherein said reaction mixture is defining a ratio eta (η) of liquid volume, in μL, to total solids, in mg, that is less than 2 μL/mg;
   said enzyme is a hydrolytic enzyme capable of catalyzing cleavage of said (CO)—O bond of an ester or carbonate linkage of said polymer; and
   B) allowing an enzyme-catalyzed reaction of said enzyme with said polymer to take place thereby forming a reaction product.

2. The method according to claim 1, wherein said polymer is in a form of powder, granule, film, cut or textile.

3. The method according to claim 1, wherein the polymer comprises at least a polyester, and/or a polycarbonate segment or chain.

4. The method according to claim 1, wherein the polymer is a polycarbonate.

5. The method according to claim 1, wherein the polymer is selected from the group consisting of polyethylene terephthalate (PET), polybutylene terephthalate (PBT), polytrimethylene terephthalate (PTT), polyethylene naphthalate (PEN), and any combination thereof.

6. The method according to claim 1, wherein the polymer is selected from the group consisting of polylactic acid or polylactide (PLA), polyglycolide (PGA), polycaprolactone (PCL), polyhydroxyalkanoate (PHA), polyhydroxybutyrate (PHB), polyethylene adipate (PEA), polybutylene succinate (PBS), and any combination thereof.

7. The method according to claim 1, wherein the polymer comprises polyethylene terephthalate (PET).

8. The method according to claim 1, wherein the enzyme is a cutinase, esterase, lipase, PET hydrolase, PETase or any combination thereof.

9. The method according to claim 1, wherein the step of combining to provide a reaction mixture comprises at least one of milling, extruding, resonance acoustic mixing, vortexing, grinding, or other methods of mixing solids, of said polymer with said enzyme and said aqueous liquid, either intermittently, or continuously.

10. The method according to claim 1, wherein the step of allowing the enzyme-catalyzed reaction to take place is as aging at a temperature of between 20° C. to 70° C.

11. The method according to claim 10, wherein said aging is for a duration of from 12 hours, and up to 30 days.

12. The method according to claim 1, wherein the method comprises conducting at least one cycle of said steps of combining to provide a reaction mixture and the step of allowing the enzyme-catalyzed reaction to take place.

13. The method according to claim 1, further comprising milling said polymer before said step of combining together the polymer with said enzyme and said aqueous liquid.

14. The method according to claim 1, wherein said reaction product comprises at least a corresponding building block of said polymer.

15. The method according to claim 1, wherein when said polymer comprises polyethylene terephthalate (PET), said monomer unit in the form of acid and/or ester comprises terephthalic acid (TPA).

16. The method according to claim 1, further comprises after step B), a step of recovering said product.

17. The method according to claim 1, wherein after step B), the method further comprises recovering the enzyme.

18. The method according to claim 7, wherein the PET has a crystallinity of at least 5%, at least 20%, or at least 30%.

19. The method according to claim 11, wherein said aging is for a duration of from 24 hours, and up to 30 days.

20. The method according to claim 12, wherein at least one of said steps of combining to provide a reaction mixture is by milling and the step of allowing the enzyme-catalyzed reaction to take place is by aging.

* * * * *